(12) United States Patent
York

(10) Patent No.: US 11,696,848 B2
(45) Date of Patent: Jul. 11, 2023

(54) SAFE SEXUAL BEHAVIOR AID

(71) Applicant: Thomas Kent York, Taipei (TW)

(72) Inventor: Thomas Kent York, Taipei (TW)

( * ) Notice: Subject to any disclaimer, the term of this patent is extended or adjusted under 35 U.S.C. 154(b) by 313 days.

(21) Appl. No.: 16/355,814

(22) Filed: Mar. 17, 2019

(65) Prior Publication Data

US 2020/0289313 A1  Sep. 17, 2020

(51) Int. Cl.
*A61F 6/04* (2006.01)

(52) U.S. Cl.
CPC .......... *A61F 6/04* (2013.01); *A61F 2006/042* (2013.01); *A61F 2006/047* (2013.01)

(58) Field of Classification Search
CPC ...... A61F 6/04; A61F 6/065; A61F 2006/042; A61F 2006/047; Y10S 128/918; A61C 5/82
See application file for complete search history.

(56) References Cited

U.S. PATENT DOCUMENTS

| | | | | |
|---|---|---|---|---|
| 4,781,709 A * | 11/1988 | Grubman | ............... | A61F 6/04 128/844 |
| 5,513,654 A * | 5/1996 | Delson | ............... | A61F 6/04 128/844 |
| 5,785,052 A * | 7/1998 | Johnson | ............... | A61F 6/04 128/830 |
| 2004/0126739 A1 * | 7/2004 | Heasley | ............... | A61C 5/82 433/136 |
| 2005/0194011 A1 * | 9/2005 | Osterberg | ............... | A61F 6/065 128/830 |
| 2008/0302367 A1 * | 12/2008 | Walker | ............... | A61F 6/06 128/830 |
| 2011/0190574 A1 * | 8/2011 | Maurette | ............... | A61F 5/41 600/38 |
| 2012/0316389 A1 * | 12/2012 | Hui | ............... | A61F 6/06 600/38 |

* cited by examiner

*Primary Examiner* — Ophelia A Hawthorne
(74) *Attorney, Agent, or Firm* — RC Trademark Company

(57) ABSTRACT

The present invention provides a safe sexual behavior aid having a main body with a first side and a second side, and the main body is formed with at least one through hole and formed with a finger sleeve portion. Accordingly, when a user uses the safe sexual behavior aid, a finger can be sleeved in the finger sleeve portion, and then the mouth and tongue contact with the first side and make oral sex with a recipient of the second side. Through the finger sleeve portion, the user can clearly distinguish the first side where the mouth and tongue contact with, and the second side where the recipient clings to; thereby achieving the effect of safe oral sex, and convenience of holding and using through effectively sleeving in the finger sleeve portion.

11 Claims, 9 Drawing Sheets

SAFE SEXUAL BEHAVIOR AID

BACKGROUND OF THE INVENTION

Field of Invention

The present invention relates to a sexual behavior aid, and more particularly to a safe sexual behavior aid with which a user can clearly identify the positions while using and is convenient to use to avoid infection of sexual diseases.

Related Art

Nowadays, the social atmosphere is open, the concept of sexual behavior between men and women has drastically escaping the constraints of traditional ethics and has become frequent, which is nothing to be surprised at. However, it has also caused easy spreading and infection of various infectious sexual diseases, skin diseases and even AIDS. Therefore, various protection methods for both men and women are constantly being proposed. However, the simplest, most effective and most ideal way is to use a condom worn by men. Since the condom can effectively prevent body fluids from coming in contact between men and women during sexual intercourse, the optimal protective effect can be achieved. Because the price is not high, easy to obtain, and it is a non-invasive device, condoms are the most common sexual behavior safety protection product at present. With sexual concepts becoming more open, the sexual behavior of oral sex is more and more common. There are products of oral sex membranes available on the market, mainly for use on private parts or anus during oral sex between male and female, or female and female. However, there are still many drawbacks in the use of oral sex membranes on the market as they exist at this time. For example, when the user makes oral sex to the recipient partner by mouth and tongue with the oral sex membrane in between, the user cannot clearly distinguish the side where the mouth and tongue have come into contact with, or the side where the recipient clings to; not to mention in the dimly lit environment this type of activity normally takes place, it is even more difficult to distinguish clearly. During a second contact, it is easy for the user to become confused with which side has been used on the recipient and as a result, have direct contact with the recipient's body fluids with the mouth and tongue. Furthermore, oral sex membrane is structurally not convenient for the user to hold, and can easily fall off during oral sex, resulting in the possibility of direct contact with the recipient. When the above situation occurs, even oral sex with the oral sex membrane cannot effectively prevent the infection of sexual diseases.

Therefore, how to improve the above-mentioned drawbacks is the technical difficulty that the inventor of the present invention wants to solve.

SUMMARY OF THE INVENTION

Therefore, in order to effectively solve the above problems, a main object of the present invention is to provide a safe sexual behavior aid with which a user can clearly identify the positions while using and is convenient to use, to avoid infection of sexual diseases.

In order to achieve the above object, the present invention provides a safe sexual behavior aid, which mainly has a main body, and the main body has a first side formed at a position of one side, and a second side formed at a position of another side. The main body is formed with at least one through hole, and the main body is formed with a finger sleeve portion on the second side. The finger sleeve portion is formed at a position opposite to the through hole and extends outward from the second side. Thereby, when a user uses the safe sexual behavior aid, a finger can be sleeved in the finger sleeve portion, and then the mouth and tongue contact with the first side and make oral sex with a recipient of the second side. Through the finger sleeve portion, the user can clearly distinguish the first side where the mouth and tongue contact with, and the second side where the recipient clings to; thereby achieving the effect of safe oral sex, and convenience of holding and using through effectively sleeving in the finger sleeve portion.

According to one embodiment of the safe sexual behavior aid of the present invention, wherein a width of an end edge of the finger sleeve portion connected to the through hole is greater than a width of an end edge away from the through hole.

According to one embodiment of the safe sexual behavior aid of the present invention, wherein the end edge of the finger sleeve portion away from the through hole is formed with an opening.

According to one embodiment of the safe sexual behavior aid of the present invention, wherein the end edge of the finger sleeve portion away from the through hole is formed with a closed end.

According to one embodiment of the safe sexual behavior aid of the present invention, wherein a sleeve ring is formed at a position of the closed end of the finger sleeve portion.

According to one embodiment of the safe sexual behavior aid of the present invention, wherein at least one anti-slip portion is formed in the finger sleeve portion.

According to one embodiment of the safe sexual behavior aid of the present invention, wherein the main body is formed with a coating on the first side.

According to one embodiment of the safe sexual behavior aid of the present invention, wherein the main body is formed with at least one protrusion on the second side.

According to one embodiment of the safe sexual behavior aid of the present invention, wherein the main body is attached with a protective layer on the first side.

According to one embodiment of the safe sexual behavior aid of the present invention, wherein the main body is composed of stretchable elastic materials such as silicone rubber or rubber or latex.

According to one embodiment of the safe sexual behavior aid of the present invention, wherein the main body is formed with a lubricating layer on the second side.

DETAILED DESCRIPTION OF THE INVENTION

Figure 1:
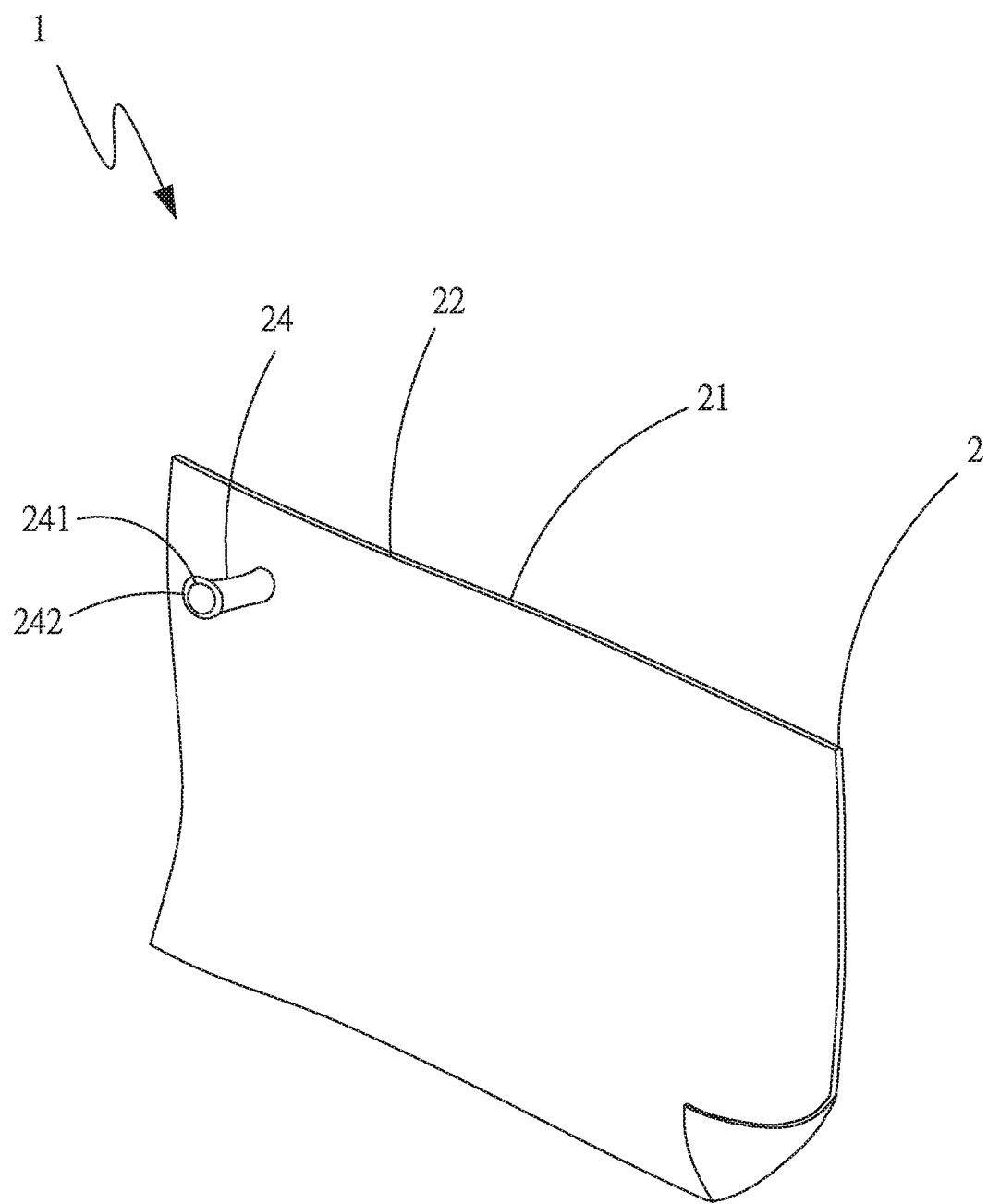
FIG. 1 is a perspective view of a preferred embodiment of the present invention.
Figure 2:
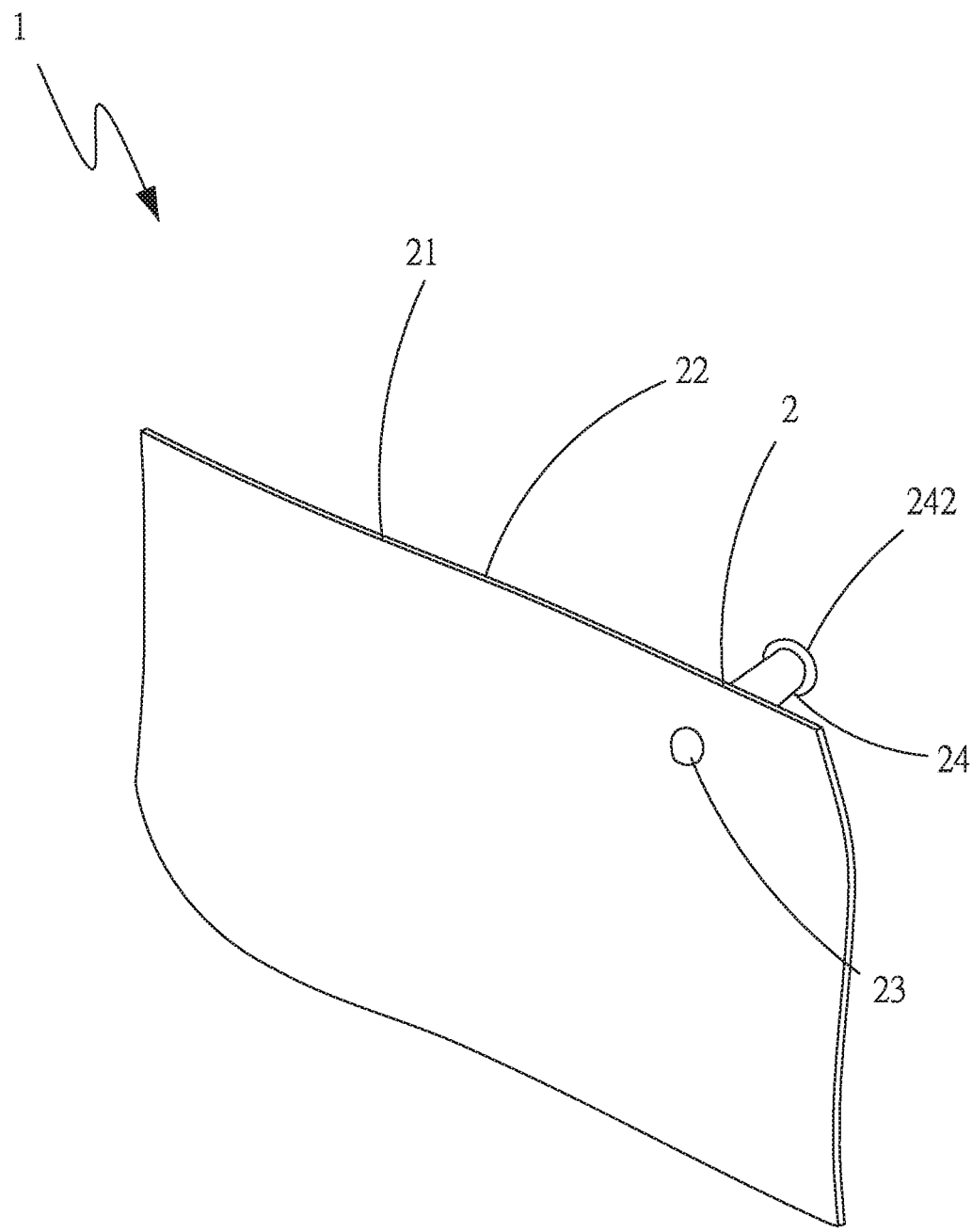
FIG. 2 is a perspective view of another angle of a preferred embodiment of the present invention.

Please refer to FIG. 1 and FIG. 2, which are perspective view and perspective view of another angle of a preferred embodiment of the present invention. It can be clearly seen from the figures that a safe sexual behavior aid 1 mainly has a main body 2 which is composed of stretchable elastic materials such as silicone rubber or rubber or latex. The main body 2 is formed with a first side 21 at a position of one side, and formed with a second side 22 at a position of another side. The main body 2 is formed with at least one through hole 23, and the main body 2 is extended with a finger sleeve portion 24, and the finger sleeve portion 24 is extending integrally and outwardly from the second side 22. The finger sleeve portion 24 is formed at a position opposite to the through hole 23, and the through hole 23 communicates with an inside of the finger sleeve portion 24. An opening 241 is formed at another end of the finger sleeve portion 24 opposite to the second side 22, and the opening 241 communicates with the through hole 23 via the finger sleeve portion 24, but a quantity of the finger sleeve portion 24 is not limited thereto. Wherein a width of an end edge of the finger sleeve portion 24 connected to the second side 22 is greater than a width of an end edge away from the second side 22, and wherein a sleeve ring 242 can be formed at a position of the opening 241.

Figure 3:
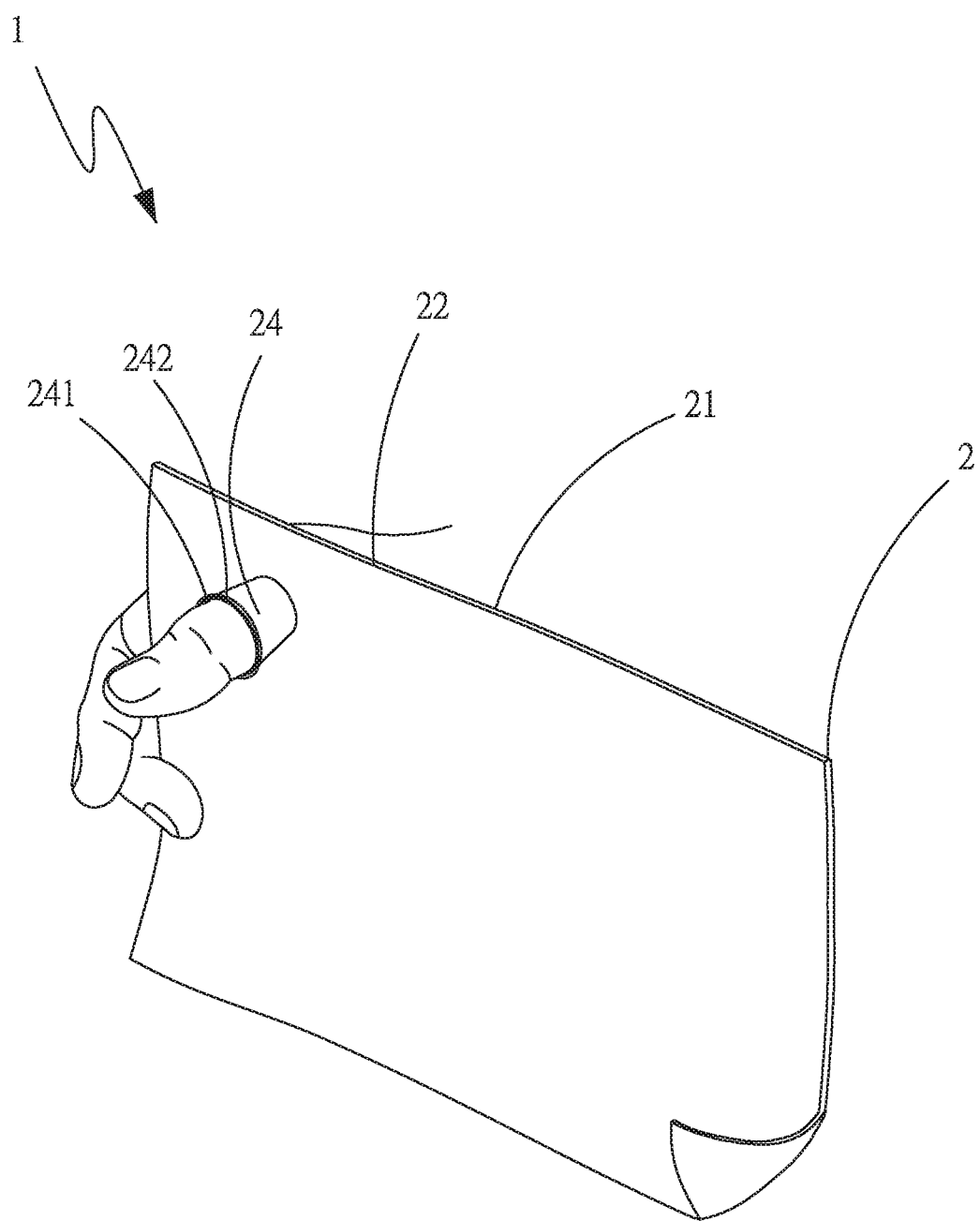
FIG. 3 is a first schematic diagram of the implementation of a preferred embodiment of the present invention.

Referring to the foregoing drawings and FIG. 3, which is a first schematic diagram of the implementation of a preferred embodiment of the present invention. It can be clearly seen from the figures that when a user uses the safe sexual behavior aid 1, a finger of the user can be sleeved in the finger sleeve portion 24 and can pass through the opening 241, wherein the main body 2 and the finger sleeve portion 24 are composed of stretchable elastic materials such as silicone rubber or rubber or latex, and therefore, when the finger is sleeved in the finger sleeve portion 24, the finger sleeve portion 24 is stretched by the finger and completely covers the finger. The user can cling the second side 22 of the main body 2 to a recipient, thereby contacting the first side 21 with mouth and tongue to make oral sex with the recipient. The user can clearly distinguish the first side 21 where the mouth and tongue contact with, and the second side 22 where the recipient clings to through the finger sleeve portion 24, thereby achieving the effect of safe oral sex, and convenience of holding and using through effectively sleeving in the finger sleeve portion 24. Wherein a width of the end edge of the finger sleeve portion 24 connected to the second side 22 is greater than a width of the end edge away from the second side 22; so that when the finger is sleeved in the finger sleeve portion 24, and passes through the opening 241, the finger sleeve portion 24 is stretched by the finger and completely covers the finger. Through the design of different widths, the body fluid of the recipient can be effectively prevented from entering the finger sleeve portion 24 from the opening 241. Wherein a sleeve ring 242 can be formed at a position of the opening 241, and the sleeve ring 242 can close the opening 241 tightly when the finger is sleeved in the finger sleeve portion 24 and passes through the opening 241, thereby effectively preventing the body fluid of the recipient from entering the finger sleeve portion 24 from the opening 241.

Figure 4:
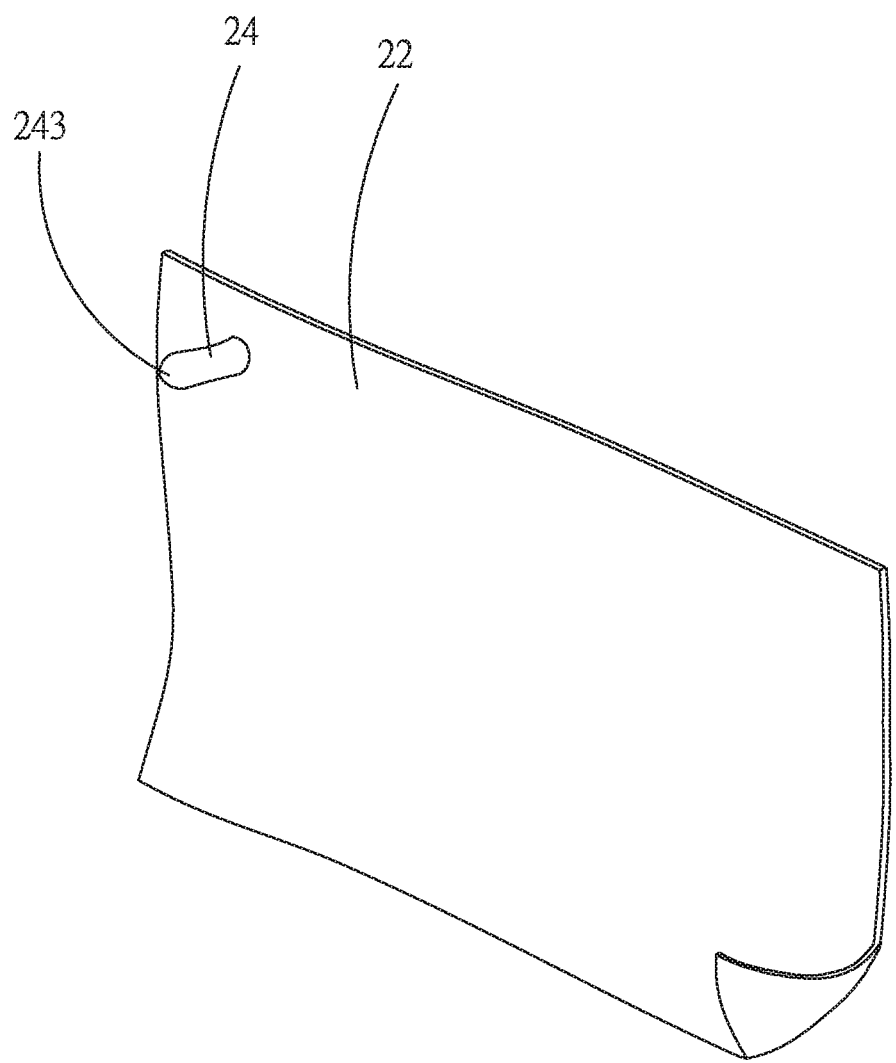
FIG. 4 is a second schematic diagram of the implementation of a preferred embodiment of the present invention.

Please refer to FIG. 4, which is a second schematic diagram of the implementation of a preferred embodiment of the present invention. Wherein the end edge of the finger sleeve portion 24 away from the second side surface 22 is formed with a closed end 243, so that when the finger is sleeved in the finger sleeve portion 24, the finger sleeve portion 24 can effectively cover the finger. Besides the effects of convenience of holding and using through effectively sleeving in the finger sleeve portion 24, the finger can be completely covered by the finger sleeve portion 24 to effectively prevent the user's finger from touching the recipient's body fluid.

Figure 5:
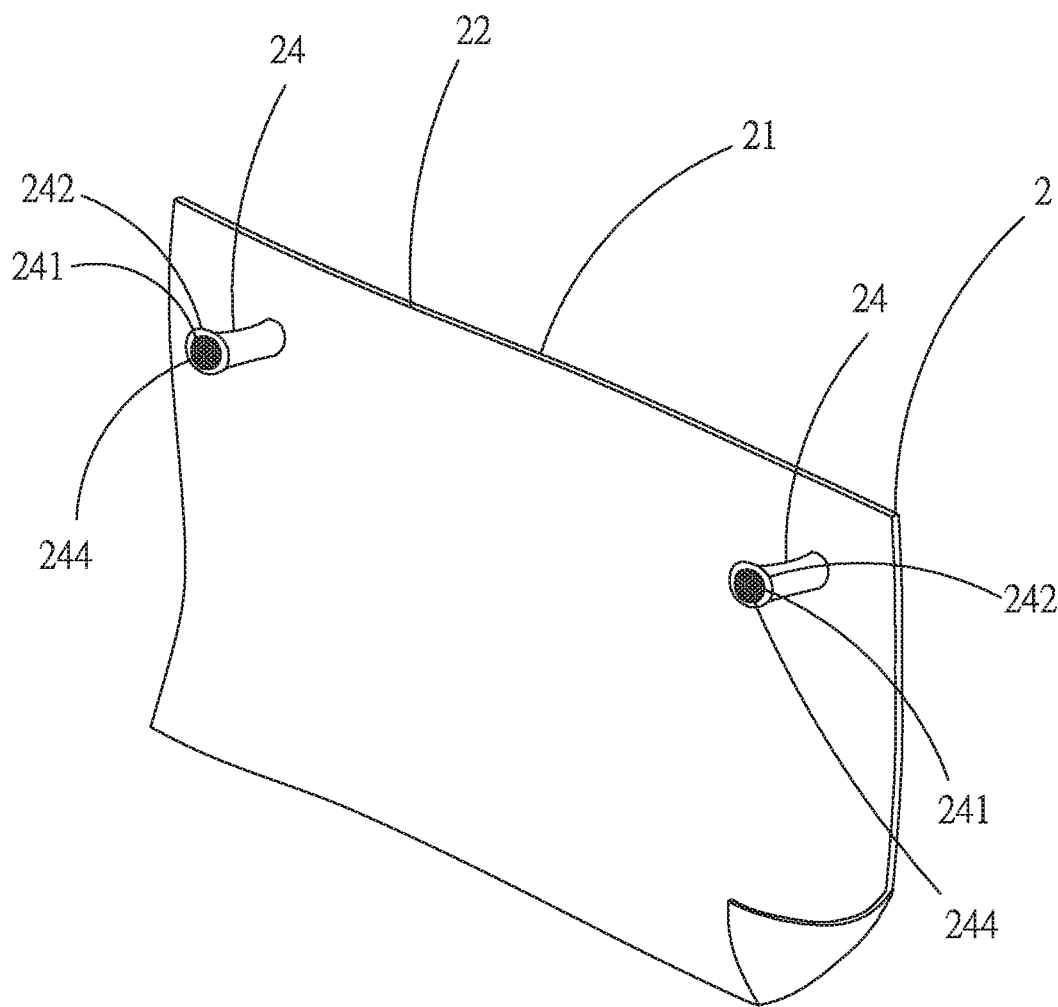
FIG. 5 is a third schematic diagram of the implementation of a preferred embodiment of the present invention.

Please refer to FIG. 5, which is a third schematic diagram of the implementation of a preferred embodiment of the present invention. Wherein at least one anti-slip portion 244 is formed in the finger sleeve portion 24, and the anti-slip portion 244 can be protruded from an inner wall of the finger sleeve portion 24, or recessed on the inner wall of the finger sleeve portion 24; so that when the finger is sleeved in the finger sleeve portion 24 to use the safe sexual behavior aid 1, the possibility of the finger detaching from the finger sleeve portion 24 can be effectively prevented. In this embodiment, two sets of the finger sleeve portions 24 are extended on the main body 2 as an implementation.

Figure 6:
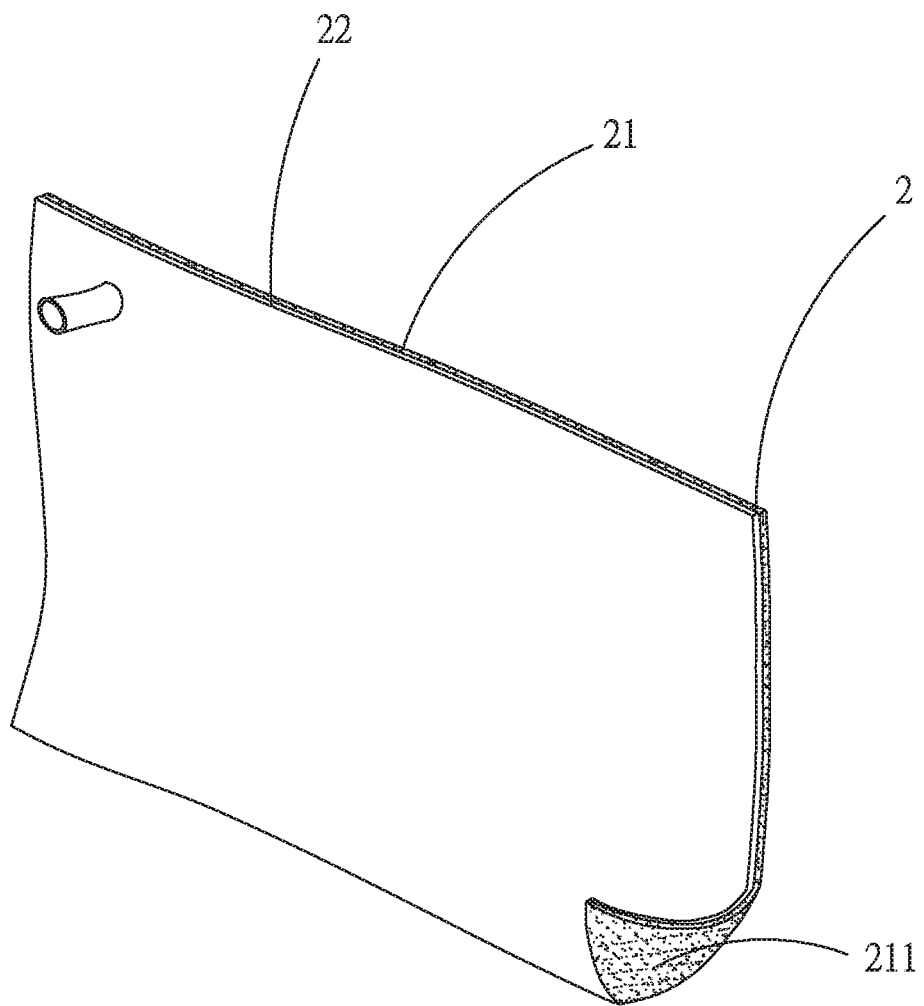
FIG. 6 is a fourth schematic diagram of the implementation of a preferred embodiment of the present invention.

Please refer to FIG. 6, which is a fourth schematic diagram of the implementation of a preferred embodiment of the present invention. Wherein the main body 2 is formed with a coating 211 on the first side 21, and the coating 211 can be a decorative pattern or an edible material; or if the decorative pattern and the edible material are simultaneously formed on the first side surface 21, the decorative pattern is mainly provided for the user to clearly distinguish the first side 21 where the mouth and tongue contact with, and the second side 22 where the recipient clings to, and the edible material is mainly provided for increasing the enjoyment and diversity of use when the user touches with the mouth and tongue.

Figure 7:
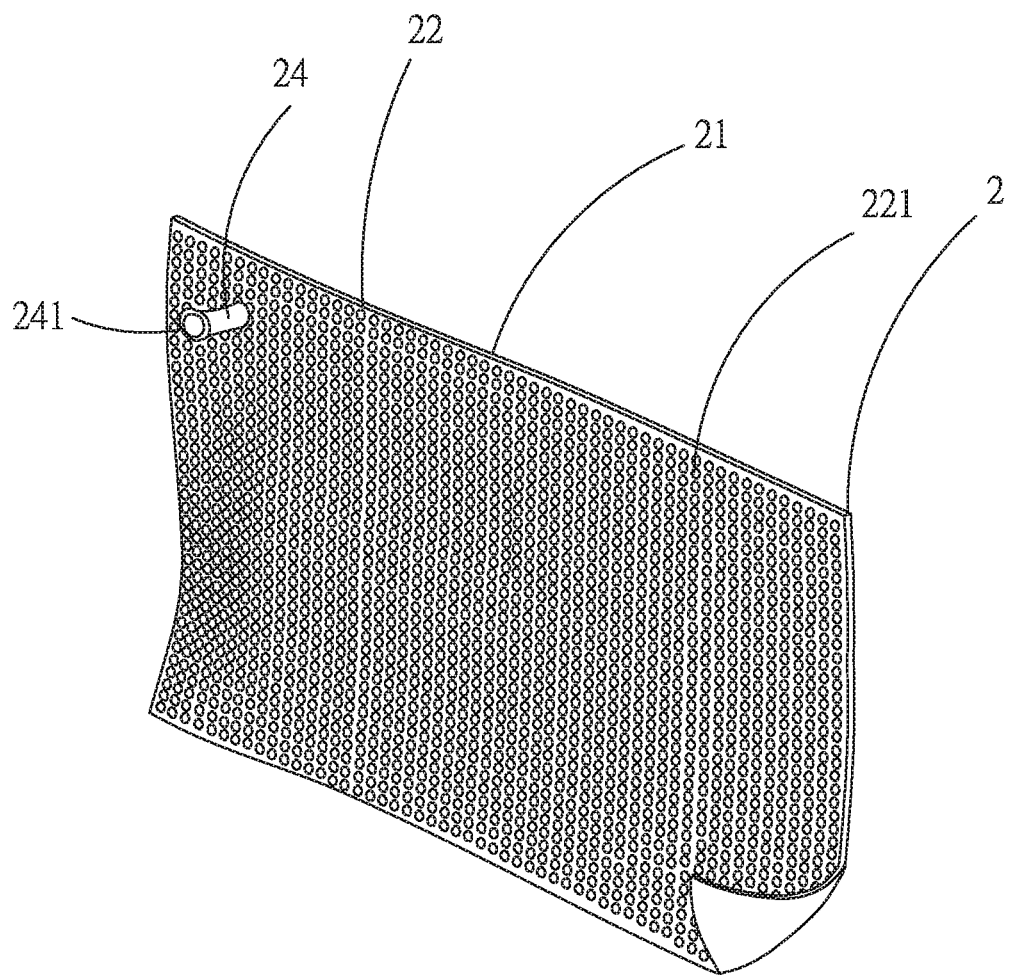
FIG. 7 is a fifth schematic diagram of the implementation of a preferred embodiment of the present invention.
Figure 8:
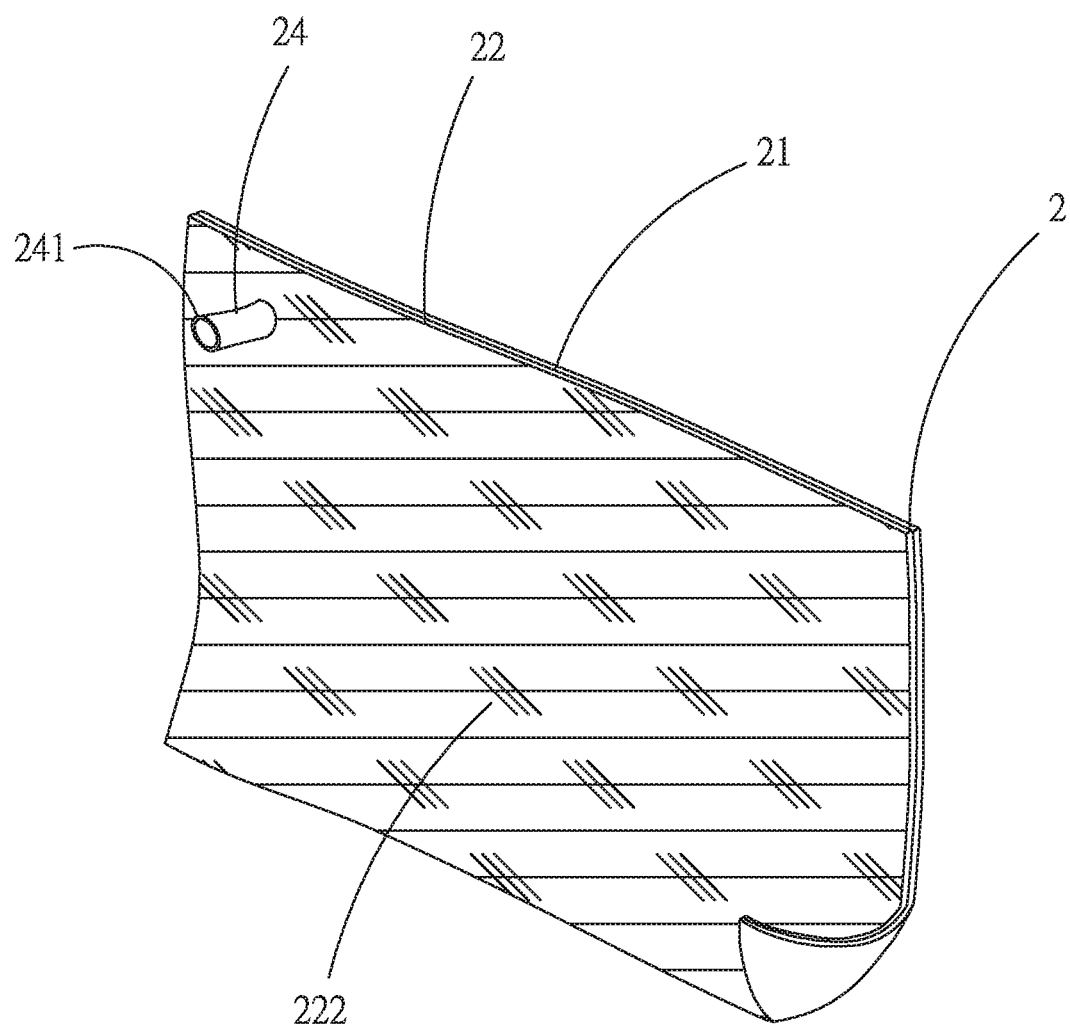
FIG. 8 is a sixth schematic diagram of the implementation of a preferred embodiment of the present invention.

Please refer to FIG. 7 and FIG. 8 at the same time, which are fifth and sixth schematic diagrams of the implementation of a preferred embodiment of the present invention. Wherein the main body 2 is formed with at least one protrusion 221 on the second side 22, so that when the second side 22 is attached to the recipient, the protrusion 221 can be used to provide an optimal tactile sensation; or a lubricating layer 222 can be formed on the second side 22 so that the lubricating layer 222 can also be used to provide an optimal tactile sensation when the second side 22 is attached to the recipient.

Figure 9:
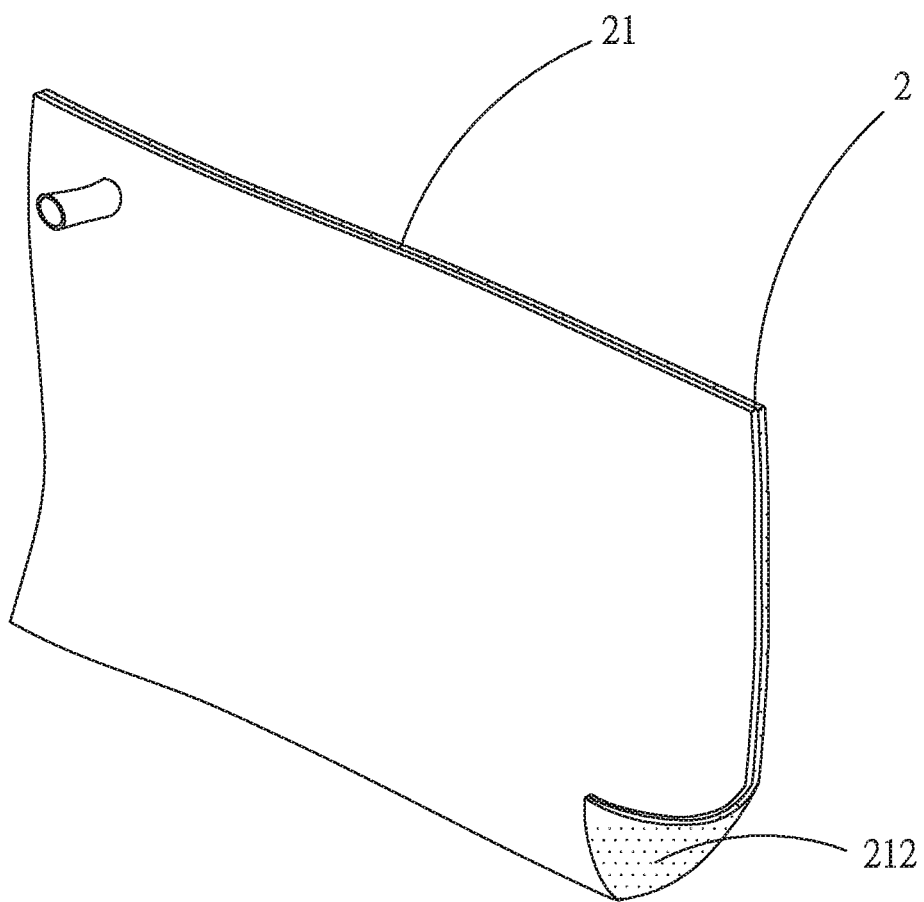
FIG. 9 is a seventh schematic diagram of the implementation of a preferred embodiment of the present invention.

Please refer to FIG. 9, which is a seventh schematic diagram of the implementation of a preferred embodiment of the present invention. Wherein the main body 2 is attached with a protective layer 212 on the first side 21, and the protective layer 212 is completely attached on the first side 21 for effectively covering the first side 21 and effectively protecting the first side 21, so that when the main body 2 is used, the protective layer 212 can be separated from the first side 21.

It is to be understood that the above description is only preferred embodiments of the present invention and is not used to limit the present invention, and changes in accordance with the concepts of the present invention may be made without departing from the spirit of the present invention, for example, the equivalent effects produced by various transformations, variations, modifications and applications made to the configurations or arrangements shall still fall within the scope covered by the appended claims of the present invention.

What is claimed is:

1. A safe sexual behavior aid, the safe sexual behavior aid comprising:
- a main body including a first side configured to be oriented away from an oral sex recipient, a second side configured to be oriented toward the oral sex recipient and a through hole disposed between the first side and the second side,
- a finger sleeve configured to be oriented away from an oral sex recipient and, located between a first corner of the second side and along a diagonal length between the first corner to an opposite second corner of the second side, where the finger sleeve extends from a position opposite to the through hole for sleeving a user's finger in the finger sleeve portion, wherein a width of an end edge of the finger sleeve connected to the second side is greater than a width of an end edge away from the second side, wherein at least one anti-slip portion is formed in the finger sleeve and, wherein the main body is formed with at least one protrusion on the second side.

2. The safe sexual behavior aid of claim 1, wherein an end edge of the finger sleeve away from the through hole is formed with an opening.

3. The safe sexual behavior aid of claim 1, wherein the end edge of the finger sleeve away from the second side is formed with a closed end.

4. The safe sexual behavior aid of claim 1, wherein a sleeve ring is formed at a position of the opening of the finger sleeve.

5. The safe sexual behavior aid of claim 1, wherein the main body is formed with at least one coating on the first side.

6. The safe sexual behavior aid of claim 1, wherein the main body is attached with a protective layer on the first side.

7. The safe sexual behavior aid of claim 1, wherein the main body is composed of stretchable elastic materials such as silicone rubber or rubber or latex.

8. The safe sexual behavior aid of claim 1, wherein the main body is formed with a lubricating layer on the second side.

9. The safe sexual behavior aid of claim 1, wherein the imaginary point of an imaginary line drawn from the first corner is one quarter of the distance between the first corner and the opposite second corner.

10. The safe sexual behavior aid of claim 1, wherein the imaginary point of the imaginary line drawn from the first corner is located at a position one quarter of a distance between the first corner and the opposite second corner.

11. The safe sexual behavior aid of claim 1, wherein the main body is rectangular shaped and the imaginary point of the imaginary line drawn from the first corner is located at a position one quarter of a distance between the first corner and the opposite second corner.

* * * * *